(12) United States Patent
Russell

(10) Patent No.: US 6,958,074 B2
(45) Date of Patent: Oct. 25, 2005

(54) RELEASABLE AND RETRIEVABLE VASCULAR FILTER SYSTEM

(75) Inventor: Scott Russell, San Jose, CA (US)

(73) Assignee: Cordis Corporation, Miami Lakes, FL (US)

( * ) Notice: Subject to any disclaimer, the term of this patent is extended or adjusted under 35 U.S.C. 154(b) by 517 days.

(21) Appl. No.: 10/040,817

(22) Filed: Jan. 7, 2002

(65) Prior Publication Data

US 2003/0130680 A1 Jul. 10, 2003

(51) Int. Cl.$^7$ ............................................. A61M 29/00
(52) U.S. Cl. ...................................... 606/200; 600/585
(58) Field of Search .................................. 606/200, 159, 606/113, 114, 127, 194; 600/585

(56) References Cited

U.S. PATENT DOCUMENTS

| | | |
|---|---|---|
| 3,435,824 A | 4/1969 | Gamponia |
| 3,889,685 A | 6/1975 | Miller, Jr. et al. |
| 3,952,747 A | 4/1976 | Kimmell, Jr. |
| 4,230,119 A | 10/1980 | Blum |
| 4,349,029 A | 9/1982 | Mott |
| 4,425,908 A | 1/1984 | Simon |
| 4,494,531 A | 1/1985 | Gianturco |
| 4,545,390 A | 10/1985 | Leary |
| 4,619,246 A | 10/1986 | Molgaard-Nielsen et al. |
| 4,619,274 A | 10/1986 | Morrison |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,793,348 A | 12/1988 | Palmaz |
| 4,794,928 A | 1/1989 | Kletschka |

(Continued)

FOREIGN PATENT DOCUMENTS

| | | |
|---|---|---|
| EP | 0 737450 A1 | 10/1996 |
| EP | 0 791 340 A1 | 8/1997 |
| FR | 2 652 267 A1 | 3/1991 |
| FR | 2 606 642 A1 | 5/1998 |
| GB | 2020557 A1 | 11/1978 |
| SU | 764684 A1 | 9/1980 |
| WO | WO 96/01591 A1 | 1/1996 |
| WO | WO 98/23322 A1 | 6/1998 |
| WO | WO 01/35857 A1 | 5/2001 |
| WO | WO 01/45592 A1 | 6/2001 |

OTHER PUBLICATIONS

A. Cragg et al., A New Percutaneous Vena Cava Filter, AJR, 141, Sep. 1983, pp. 601–604.

(Continued)

*Primary Examiner*—Julian W. Woo
*Assistant Examiner*—Victor Nguyen
(74) *Attorney, Agent, or Firm*—Carl J. Evens (57) ABSTRACT

A releasable and retrievable vascular filter system comprising a filter, a porous filter membrane attached to the filter, and an anti-migration feature for causing the filter to remain substantially stationary in the lumen of the vessel during the clinical procedure. The releasable and retrievable vascular filter system minimizes or substantially eliminates filter movement during the procedure, which may result in damage to the lumen, and/or the release of embolic particulates captured within the filter. The releasable and retrievable vascular filter system also allows for guidewire exchanges, which may be necessary for successful completion of the clinical procedure.

17 Claims, 9 Drawing Sheets

U.S. PATENT DOCUMENTS

| | | |
|---|---|---|
| 4,832,055 A | 5/1989 | Palestrant |
| 4,842,579 A | 6/1989 | Shiber |
| 4,873,978 A | 10/1989 | Ginsburg |
| 4,884,573 A | 12/1989 | Wajay et al. |
| 4,921,484 A | 5/1990 | Hillstead |
| 4,926,858 A | 5/1990 | Gifford, III et al. |
| 4,957,501 A | 9/1990 | Lahille et al. |
| 4,969,891 A | 11/1990 | Gewertz |
| 4,990,156 A | 2/1991 | Lefebvre |
| 5,011,488 A | 4/1991 | Ginsburg |
| 5,053,008 A | 10/1991 | Bajaj |
| 5,059,205 A | 10/1991 | El-Nounou et al. |
| 5,092,839 A | 3/1992 | Kipperman |
| 5,095,915 A | 3/1992 | Engelson |
| 5,108,419 A | 4/1992 | Reger et al. |
| 5,133,733 A | 7/1992 | Rasmussen et al. |
| 5,152,777 A | 10/1992 | Goldberg et al. |
| 5,190,540 A | 3/1993 | Lee |
| 5,190,546 A | 3/1993 | Jervis |
| 5,201,757 A | 4/1993 | Heyn et al. |
| 5,242,462 A | 9/1993 | El-Nounou et al. |
| 5,279,546 A | 1/1994 | Mische et al. |
| 5,324,304 A | 6/1994 | Rasmussen |
| 5,329,942 A | 7/1994 | Gunther et al. |
| 5,413,586 A | 5/1995 | Dibie et al. |
| 5,421,832 A | 6/1995 | Lefebvre |
| 5,496,277 A | 3/1996 | Termin et al. |
| 5,531,788 A | 7/1996 | Dibie et al. |
| 5,549,626 A | 8/1996 | Miller et al. |
| 5,632,760 A | 5/1997 | Sheiban et al. |
| 5,662,631 A | 9/1997 | Marx |
| 5,662,671 A | 9/1997 | Barbut et al. |
| 5,681,347 A | 10/1997 | Cathcart et al. |
| 5,695,519 A | 12/1997 | Summers et al. |
| 5,709,704 A | 1/1998 | Nott et al. |
| 5,749,890 A | 5/1998 | Shaknovich |
| 5,769,816 A | 6/1998 | Barbut et al. |
| 5,779,716 A | 7/1998 | Cano et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,836,969 A | 11/1998 | Kim et al. |
| 5,848,964 A | 12/1998 | Samuels |
| 5,876,367 A | 3/1999 | Kaganov et al. |
| 5,902,263 A | 5/1999 | Patterson et al. |
| 5,910,154 A | 6/1999 | Tsugita et al. |
| 5,944,728 A * | 8/1999 | Bates .......................... 606/127 |
| 6,001,118 A * | 12/1999 | Daniel et al. ............... 606/200 |
| 6,013,093 A | 1/2000 | Nott et al. |
| 6,051,014 A | 4/2000 | Jang |
| 6,053,932 A | 4/2000 | Daniel et al. |
| 6,059,814 A | 5/2000 | Ladd |
| 6,059,825 A | 5/2000 | Hobbs et al. |
| 6,074,357 A | 6/2000 | Kaganov et al. |
| 6,080,178 A | 6/2000 | Meglin |
| 6,126,673 A | 10/2000 | Kim et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,604 B1 | 1/2001 | Cano |
| 6,179,859 B1 | 1/2001 | Bates et al. |
| 6,179,861 B1 | 1/2001 | Khosravi et al. |
| 6,187,015 B1 | 2/2001 | Brenneman |
| 6,203,561 B1 | 3/2001 | Ramee et al. |
| 6,214,025 B1 | 4/2001 | Thistle et al. |
| 6,221,096 B1 | 4/2001 | Aiba et al. |
| 6,241,746 B1 | 6/2001 | Bosma et al. |
| 6,258,115 B1 | 7/2001 | Dubrul |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,290,710 B1 | 9/2001 | Cryer et al. |
| 6,336,934 B1 | 1/2002 | Gilson et al. |
| 6,346,116 B1 | 2/2002 | Brooks et al. |
| 6,500,182 B2 * | 12/2002 | Foster .......................... 606/127 |

OTHER PUBLICATIONS

A. Cragg et al., Nonsurgical Placement of Arterial Endoprosthesis; A New Technique Using Nitinol Wire, AJR, Apr. 1983, p. 261–263.

Eichelter, et al., Prophylaxis of Pulmonary Embolism, Archives of Surgery, vol. 97, Aug. 1968, p. 348 et seq.

G. Lund et al., Long–Term Patency of the Ductus Arteriosus After Balloon Dilatation: An Experimental Study, AJR Sep. 1983, p. 772.

Greenfield, et al., A New Intercaval Filter Permitting Continued Flow and Resolution of Emboli, Surgery, vol. 73, No. 4, pp. 599–606.

M. H. Wholey et al, PTA and Stents in the Treatment of Extraclavical Circulation, Journal of Advanced Cardiology vol. 9 Suppl. E. 1996, pp. 25E–30E.

Topol, Eric J., et al. Recognition of the Importance of Embolization in Atherosclerotic Vascular Disease American Heart Journal 2000.

European Search Report dated Jul. 25, 2003 for corresponding Appln. No. EP 03 25 0037.

* cited by examiner

RELEASABLE AND RETRIEVABLE VASCULAR FILTER SYSTEM

I. FIELD OF THE INVENTION

This invention relates to the treatment of vascular disease, and more particularly to a vascular filter system for use during medical procedures.

II. BACKGROUND OF THE INVENTION

Percutaneous transluminal coronary angioplasty (PTCA), stenting and atherectomy are therapeutic medical procedures used to increase blood flow through the coronary arteries. These procedures may often be performed as alternatives to coronary bypass surgery. Percutaneous transluminal angioplasty (PTA) and stenting may often be performed as alternatives to carotid endarterectomy, and femoral-popliteal bypass procedures. In PTCA or PTA procedures, the angioplasty balloon is inflated within the stenosed vessel, at the location of an occlusion, in order to shear and disrupt the wall components of the vessel to obtain an enlarged lumen. In stenting, an endoluminal prosthesis is implanted in the vessel to maintain patency following the procedure. In atherectomy, a rotating blade is used to shear plaque from the arterial wall.

One of the complications associated with all these techniques is the accidental dislodgment of plaque, thrombus or other embolic particulates generated during manipulation of the vessel, thereby potentially causing occlusion of the narrower vessels downstream, which may lead to ischemia or infarct of the organ which the vessel supplies. Such emboli may be extremely dangerous to the patient, and may result in myocardial infarction, stroke or limb ischemia. In 1995, Waksman et al. disclosed that distal embolization is common after directional atherectomy in coronary arteries and saphenous vein grafts. See Waksman et al., American Heart Journal 129(3): 430–5 (1995). This study found that distal embolization occurs in 28 percent (31 out of 111) of the patients undergoing atherectomy. In January 1999, Jordan, Jr. et al. disclosed that treatment of carotid stenosis using percutaneous angioplasty with stenting procedure is associated with more than eight times the rate of microemboli seen using carotid endarterectomy. See Jordan, Jr. et al. Cardiovascular Surgery 7(1): 33–8 (1999). Microemboli, as detected by transcranial Doppler monitoring in this study, have been shown to be a potential cause of stroke. The embolic materials include calcium, intimal debris, atheromatous plaque, and thrombi.

Vascular filters are also well known in the art, especially vena cava filters, as illustrated in U.S. Pat. Nos. 4,727,873 and 4,688,553. There is also a substantial amount of medical literature describing various designs of vascular filters and reporting the results of clinical and experimental use thereof. See, for example, the article by Eichelter and Schenk, entitled "Prophylaxis of Pulmonary Embolism," Archives of Surgery, Vol. 97 (August, 1968). See, also, the article by Greenfield, et al; entitled "A New Intracaval Filter Permitting Continued Flow and Resolution of Emboli," Surgery, Vol. 73, No. 4 (1973).

Vascular filters are often used during a postoperative period, when there is a perceived risk of a patient encountering pulmonary embolism resulting from clots generated peri-operatively. Pulmonary embolism is a serious and potentially fatal condition that occurs when these clots travel to the lungs. The filter is therefore typically placed in the vena cava to catch and trap clots before they can reach the lungs.

Many of the vascular filters in the prior art are intended to be permanently placed in the venous system of the patient, so that even after the need for the filter has passed, the filter remains in place for the life of the patient. U.S. Pat. No. 3,952,747 describes a stainless steel filtering device that is permanently implanted transvenously within the inferior vena cava. This device is intended to treat recurrent pulmonary embolism. Permanent implantation is often deemed medically undesirable, but it is done because filters are implanted in patients in response to potentially life-threatening situations.

To avoid permanent implantation, it is highly desirable to provide an apparatus and method for preventing embolization associated with angioplasty, stenting or other procedures. In particular, it is desirable to provide a device that may be temporarily placed within the vascular system to collect and retrieve plaque, thrombus and other embolic particulates that have been dislodged during angioplasty, stenting or other procedures. Such a device is removed at the end of the procedure. U.S. Pat. Nos. 6,179,861 and 6,001,118 describe guidewire-based filters where the filter resembles a windsock and is supported by one or more articulated support hoops. U.S. Pat. Nos. 5,814,064 and 5,827,324 describe guidewire-based filter devices, wherein the filter is expanded to a predetermined diameter through the introduction of a fluid or a gas. U.S. Pat. Nos. 6,168,604 and 6,152,946 describe guidewire-based filters, wherein the diameter of the filter is controlled by advancing and retracting a sheath over the filter component.

Notwithstanding the usefulness of the above-described methods, one concern commonly encountered with these devices is that the filter may move when the guidewire moves, thereby causing potential damage to the lumen, and risking the release of embolic particulates had been captured during the procedure. Another concern commonly encountered with these devices is that the filter and the guidewire are a single unit. Therefore, guidewire exchanges, which may be necessary for successful completion of the clinical procedure, cannot be performed.

The prior art has yet to disclose, and a need still exists for, a vascular filter system which may be used to address the clinical problem of minimizing or substantially eliminating movement of the filter during the clinical procedure. The prior art has also not yet disclosed, and a need still exists for, a vascular filter which may be used to address the problem of allowing guidewires exchanges, which may be necessary for successful completion of the clinical procedure.

III. SUMMARY OF THE INVENTION

The present invention provides a releasable and retrievable vascular filter system, which may be used to address the clinical problems of minimizing or substantially eliminating movement of the filter during the clinical procedure, and allowing guidewire exchanges, which may be necessary for successful completion of the clinical procedure, as briefly described above.

An objective of the invention is to provide a releasable and retrievable vascular filter system which places an untethered filter into the lumen of the vessel, in a position distal to the occlusion or to the location of the necessary intervention, which will remain stationary during the procedure. The filter system comprises a filter with an anti-migration feature, a deployment and release mechanism, and a retrieval device. The filter deployment and release mechanism allows for proper filter placement within the lumen. The deployment mechanism also allows the filter to expand to its second larger diameter, which is substantially equal to the diameter of the lumen, and to be placed in a generally sealing relationship with the lumen. The anti-migration feature allows the filter to remain substantially stationary in the lumen of a vessel during the procedure. The filter is untethered by a guidewire, and therefore does not move when the guidewire moves. The filter remains in place, capturing embolic particulates that may be released during the procedure. Another objective of the invention is to allow guidewire exchanges to be performed throughout the procedure, as needed, without disturbing or moving the filter. Then, a retrieval device is utilized for recapturing, collapsing and removing the filter from the lumen, with the embolic particulates captured within the filter.

In accordance with one aspect, the present invention is directed to a releasable and retrievable vascular filter system for insertion into a lumen of a vessel, comprising a vascular filter with a smaller first diameter for insertion into the lumen and a larger second diameter for expanding to a diameter substantially equal to the diameter of the lumen and to be placed in a generally sealing relationship with the lumen. The system further comprises a porous filter membrane attached to the filter, a deployment and release mechanism for causing the filter to be positioned in the lumen of the vessel and to achieve the second larger diameter, an anti-migration feature for causing the filter to remain stationary in the lumen, and a retrieval device for recapturing the filter, for causing the filter to achieve the smaller first diameter, and for removing the filter from the lumen.

In accordance with another aspect, the present invention is directed to a releasable and retrievable vascular filter system for insertion into a lumen of a vessel, wherein the deployment and release mechanism comprises a storage tube having a proximal end, a distal end, and an inner lumen, with the distal end of the filter slidably insertable into the proximal end of the storage tube.

The deployment and release mechanism further comprises a catheter having a proximal end, a distal end, and an inner lumen, with the distal end of the storage tube containing the filter slidably insertable into the proximal end of the catheter. The deployment and release mechanism further comprises an obdurator having an outer diameter, a proximal end and a distal end, with the distal end of the obdurator slidably insertable into the proximal end of the storage tube until the distal end of the obdurator is substantially in contact with the proximal end of the filter, and the obdurator is positioned to push the filter into the proximal end of the catheter, through the lumen of the catheter, and out of the distal end of the catheter.

In accordance with another aspect, the present invention is directed to a releasable and retrievable vascular filter system for insertion into a lumen of a vessel, wherein the deployment and release mechanism comprises a catheter having a proximal end, a distal end, and an inner lumen. The deployment and release mechanism further comprises a shaft having an outer diameter, a proximal end and a distal end, with the filter releasably attached near the distal end of the shaft, and the catheter coaxially disposed around the shaft and the filter, such that the catheter may be slidably retracted to deploy the filter.

In accordance with another aspect, the present invention is directed to a releasable and retrievable vascular filter system for insertion into a lumen of a vessel, wherein the deployment and release mechanism comprises a guidewire, with the proximal end of the filter releasably attachable near and detachable from the distal end of the guidewire. The deployment and release mechanism further comprises a catheter having a proximal end, a distal end, and an inner lumen, with the proximal end of the guidewire slidaby insertable into the distal end of the catheter until the catheter is coaxially disposed around the guidewire and the filter, and the catheter may be slidably retracted to deploy the filter.

In accordance with another aspect, the present invention is directed to a releasable and retrievable vascular filter system for insertion into a lumen of a vessel, wherein the anti-migration feature comprises the chronic outward force of Nickel-Titanium alloy.

In accordance with another aspect, the present invention is directed to a releasable and retrievable vascular filter system for insertion into a lumen of a vessel, wherein the anti-migration feature comprises hooks attached to the filter.

In accordance with another aspect, the present invention is directed to a releasable and retrievable vascular filter system for insertion into a lumen of a vessel, wherein the anti-migration feature comprises the frictional force of the geometric design of the struts.

In accordance with another aspect, the present invention is directed to a releasable and retrievable vascular filter system for insertion into a lumen of a vessel, wherein the anti-migration feature comprises a friction coating on the filter.

In accordance with another aspect, the present invention is directed to a releasable and retrievable vascular filter system for insertion into a lumen of a vessel, wherein the anti-migration feature comprises a surface treatment that increases the friction coefficient of the filter.

In accordance with another aspect, the present invention is directed to a releasable and retrievable vascular filter system for insertion into a lumen of a vessel, wherein the retrieval device comprises a snare, and the filter comprises a snareable feature.

In accordance with another aspect, the present invention is directed to a releasable and retrievable vascular filter system for insertion into a lumen of a vessel, wherein the retrieval device comprises a wire having an outer diameter, a proximal end and a distal end, a hook attached near the distal end of the wire, and a hook attached near the proximal end of the filter.

In accordance with another aspect, the present invention is directed to a releasable and retrievable vascular filter system for insertion into a lumen of a vessel, wherein the retrieval device comprises a wire having an outer diameter, a proximal end and a distal end, a ball attached near the distal end of the wire, and a receiver attached near the proximal end of the filter.

In accordance with another aspect, the present invention is directed to a releasable and retrievable vascular filter system for insertion into a lumen of a vessel, wherein the retrieval device comprises a guidewire detachable from and attachable to the filter.

An advantage of the present invention is that the anti-migration feature of the filter causes it to remain stationary in the lumen during the procedure, thereby minimizing the risk of potential damage to the lumen, and minimizing the risk of releasing embolic particulates which had been captured during the procedure. Another advantage of the present invention is that the filter and the guidewire are not a single unit, so the operator may freely exchange guidewires, which may be necessary for successful completion of the clinical procedure. Given the following enabling description of the drawings, the apparatus should become evident to a person of ordinary skill in the art.

IV. BRIEF DESCRIPTION OF THE DRAWINGS

The foregoing and other aspects of the present invention will best be appreciated with reference to the detailed description of the invention in conjunction with the accompanying drawings, wherein.

V. DETAILED DESCRIPTION OF THE DRAWINGS

The releasable and retrievable vascular filter system of the present invention is designed to address the clinical problem of movement of the filter when the guidewire moves, thereby causing potential damage to the lumen, and risking the release of embolic particulates which were captured during the procedure. The releasable and retrievable vascular filter system of the present invention is also designed to address the need to exchange guidewires, which may be necessary for successful completion of the clinical procedure. Guidewire exchanges may be necessary because different guidewire characteristics may be needed during different portions of the clinical procedure. For example, guidewire torqueability and steerability may be required at the beginning of the procedure, in order to access the site of the occlusion or necessary intervention. Then, extra support may be required later in the procedure, when the guidewire is needed to serve as a conduit for other procedural devices.

The releasable and retrievable vascular filter system comprises a vascular filter with a smaller first diameter for insertion into the lumen and a larger second diameter for expanding to a diameter substantially equal to the diameter of the lumen and to be placed in a generally sealing relationship with the lumen. The system further comprises a porous filter membrane attached to the filter, a deployment and release mechanism for causing the filter to be positioned in the lumen of the vessel and to achieve the second larger diameter, an anti-migration feature for causing the filter to remain stationary in the lumen, and a retrieval device for recapturing the filter, for causing the filter to achieve the smaller first diameter, and for removing the filter from the lumen. The deployment and release mechanism is utilized to place the filter in the lumen of the vessel, in a position distal to the occlusion or to the location of the necessary intervention. The deployment and release mechanism also allows the filter to expand to its second larger diameter, which substantially equals the diameter of the lumen, and to be placed in a generally sealing relationship with the lumen. The anti-migration feature allows the filter to remain substantially stationary in the lumen of a vessel during the procedure. The filter is untethered by a guidewire, and therefore does not move when the guidewire moves. The filter remains in place, capturing embolic particulates which may be released during the procedure. Then, a retrieval device is utilized for recapturing, collapsing and removing the filter from the lumen, with the embolic particulates captured within the filter.

Figure 1:
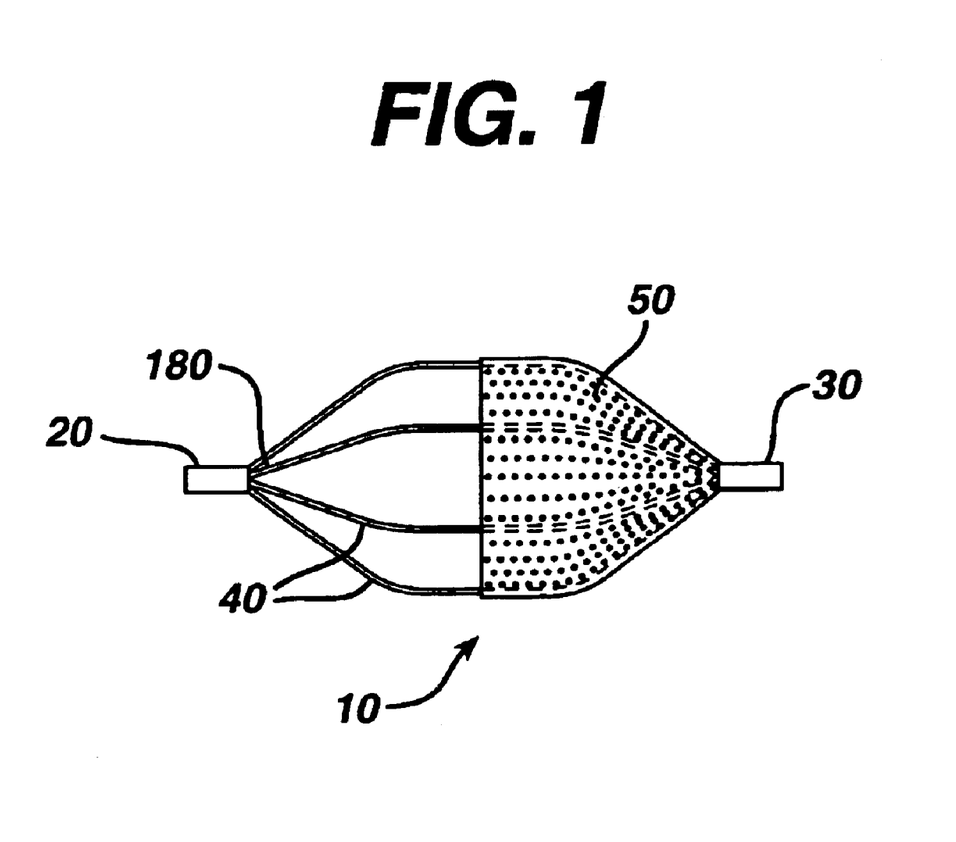
FIG. 1 illustrates a partial, enlarged cross-sectional view of an exemplary embodiment of the releasable and retrievable vascular filter system, with the filter in the expanded position and the anti-migration feature comprising the chronic outward force of the Nickel-Titanium alloy, in accordance with the present invention.

While the present invention may be realized in a number of exemplary embodiments, for ease of explanation, one exemplary embodiment will be described in detail. Referring to the figures wherein like numerals indicate the same element throughout the views, there is shown in FIG. 1 a releasable and retrievable vascular filter system made in accordance with the present invention. The releasable and retrievable vascular filter system comprises a filter 10, having a proximal end 20, a distal end 30, and a plurality of struts 40 extending therebetween. The filter further comprises a porous filter membrane 50 attached to the filter distal end 30 and to the plurality of struts 40. The porous filter membrane 50 may have a length that is less than the length of the plurality of struts 40. The filter has a smaller first diameter for insertion into the lumen, and a larger second diameter, as illustrated in FIG. 1, for expanding to a diameter substantially equal to the diameter of the lumen and to be placed in a generally sealing relationship with the lumen. The filter further comprises an anti-migration feature, which causes the filter 10 to remain substantially stationary in the lumen. In this exemplary embodiment, the anti-migration feature comprises the chronic outward force of the Nickel-Titanium material from which the filter may be made.

Figure 2:
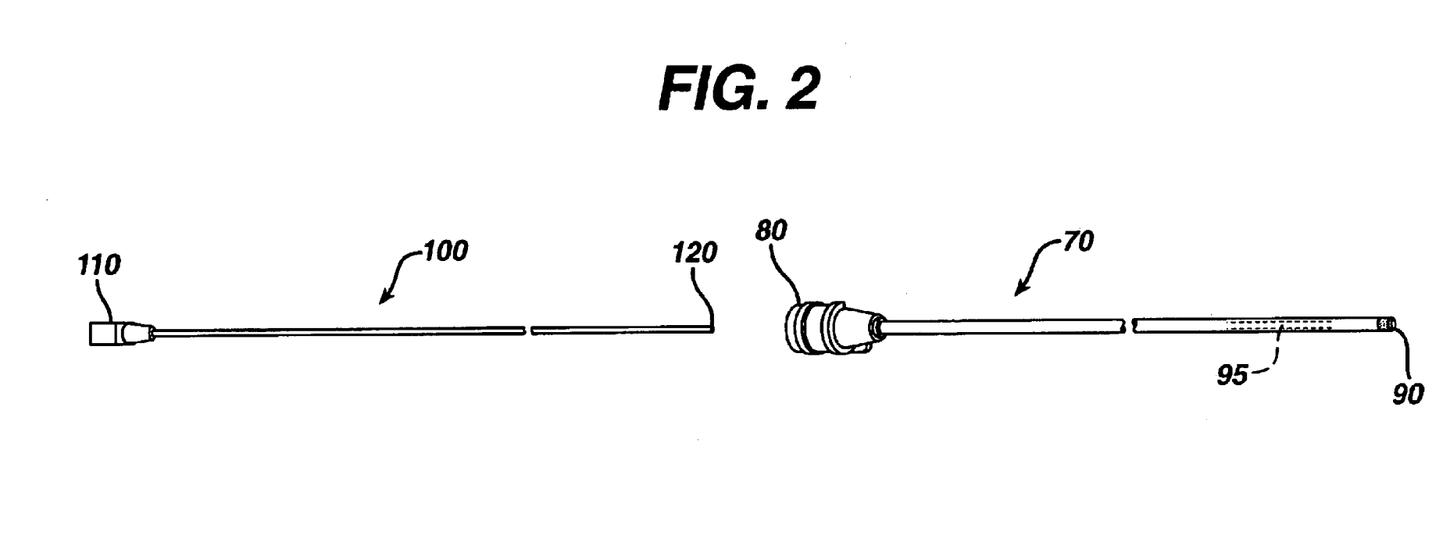
FIG. 2 illustrates a partial, cross-sectional view of an exemplary embodiment of the releasable and retrievable vascular filter system, with the deployment and release mechanism comprising a catheter and obdurator, in accordance with the present invention.
Figure 3:
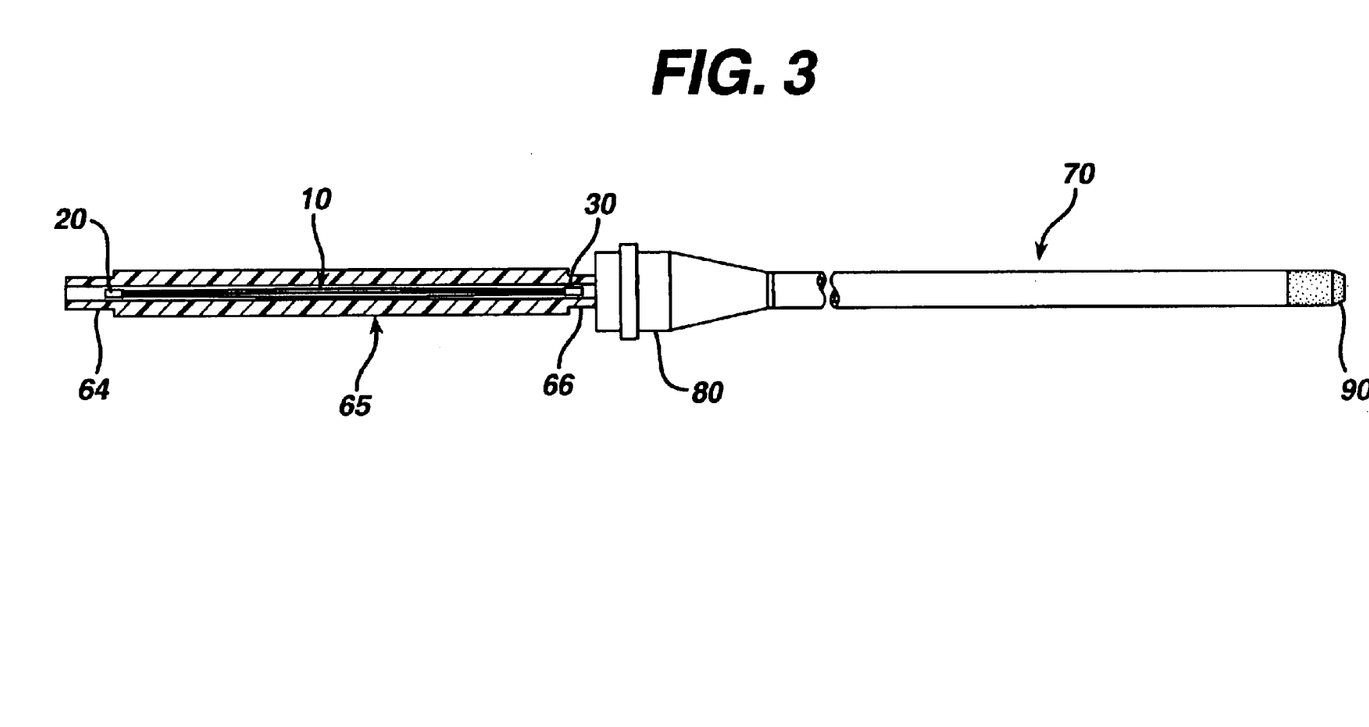
FIG. 3 illustrates a partial, cross-sectional view of an exemplary embodiment of the releasable and retrievable vascular filter system, with the storage tube and filter being inserted into the catheter, in accordance with the present invention.
Figure 4A:
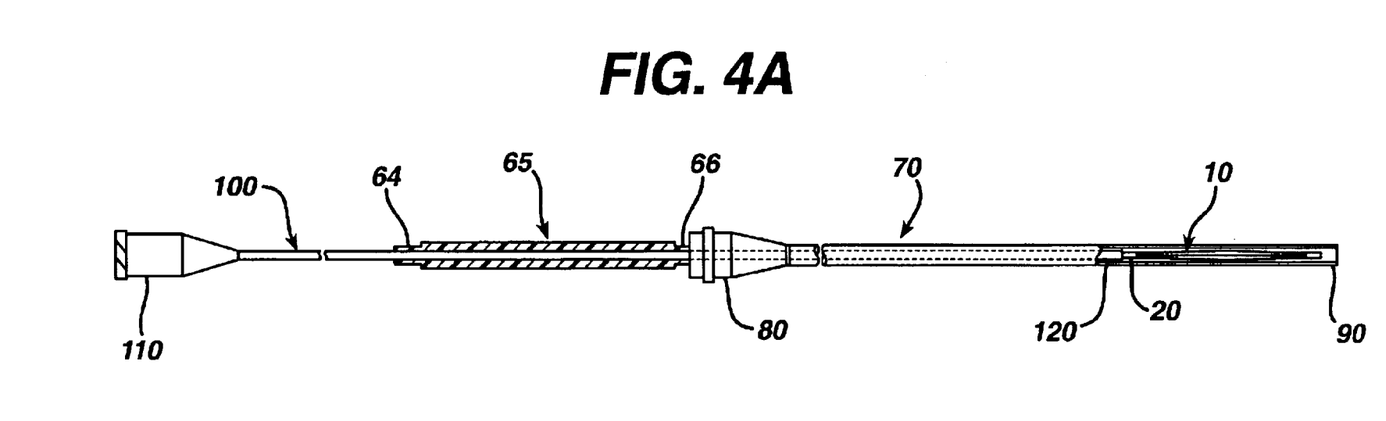
FIG. 4A and FIG. 4B illustrate partial, cross-sectional views of an exemplary embodiment of the releasable and retrievable vascular filter system, with the obdurator pushing the filter out of the catheter, in accordance with the present invention.
Figure 4B:
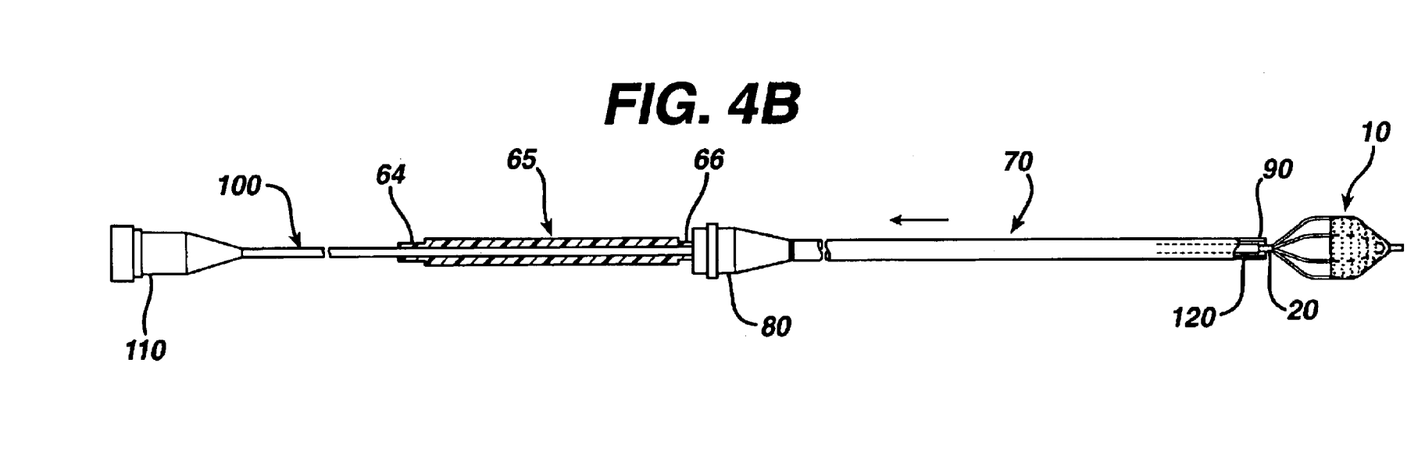

The releasable and retrievable vascular filter system further comprises a deployment and release mechanism for causing the filter to be positioned in the lumen of the vessel and for causing the filter to achieve its second larger diameter. In this exemplary embodiment, the deployment and release mechanism comprises a catheter 70, as shown in FIG. 2, with a proximal end 80, a distal end 90 and an inner lumen 95. The deployment and release mechanism further comprises an obdurator 100, having a proximal end 110 and a distal end 120, with the distal end 120 slidably insertable into the proximal end of the catheter 80. As illustrated in FIG. 3, the releasable and retrievable vascular filter system further comprises a storage tube 65, having a proximal end 64 and a distal end 66. The distal end 30 of the filter 10, in the collapsed state, may be slidably inserted into the proximal end 64 of the storage tube, and advanced until the storage tube 65 is coaxially disposed around the filter 10, as illustrated in FIG. 3. Then, the distal end of the storage tube 66 is slidably inserted into the proximal end of the catheter 80. At this point, as illustrated in FIG. 4, the distal end 120 of the obdurator 100 may be slidably inserted into the proximal end 64 of the storage tube 65 and advanced until the distal end of the obdurator 120 is substantially in contact with the proximal end of the filter 20. The obdurator is then advanced further until the filter 10 is pushed into the proximal end of the catheter 80, through the catheter 70, as illustrated in FIG. 4A, and then out of the distal end of the catheter 90, as illustrated in FIG. 4B. The filter 10 then expands to achieve the second larger diameter, as illustrated in FIG. 4B, and is positioned in the lumen, with the chronic outward force of the Nickel-Titanium alloy, from which the filter may be made, causing the filter 10 to remain stationary in the lumen.

Figure 5A:
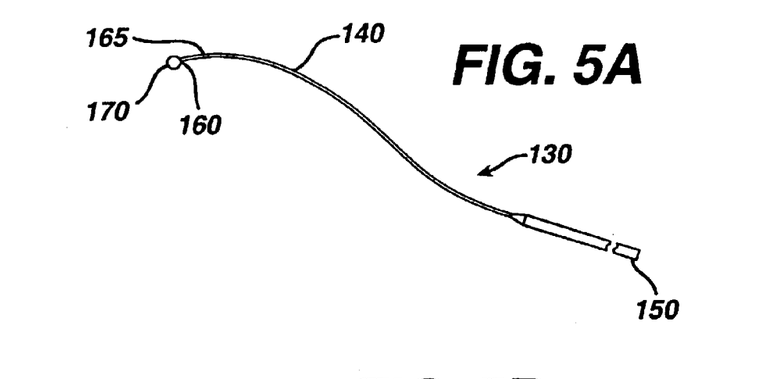
FIGS. 5A, 5B, 5C and 5D illustrate partial, enlarged, cross-sectional views of an exemplary embodiment of the releasable and retrievable vascular filter system, using a ball hook retrieval system, in accordance with the present invention.
Figure 5B:
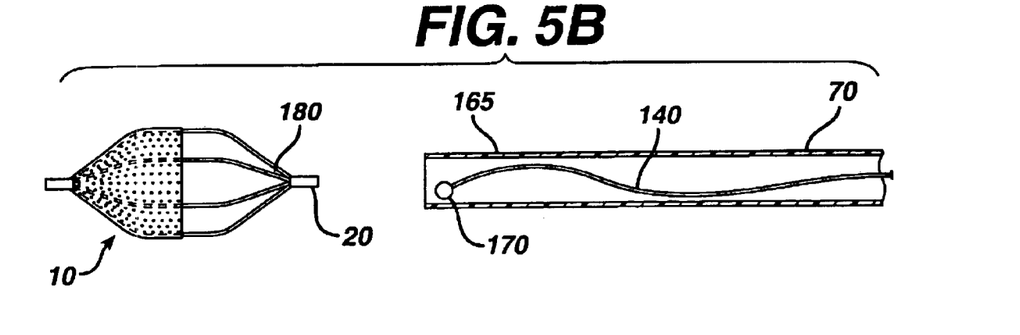
Figure 5C:
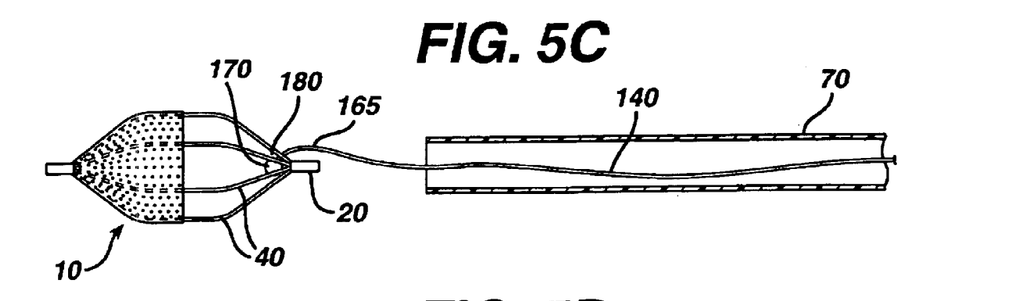
Figure 5D:
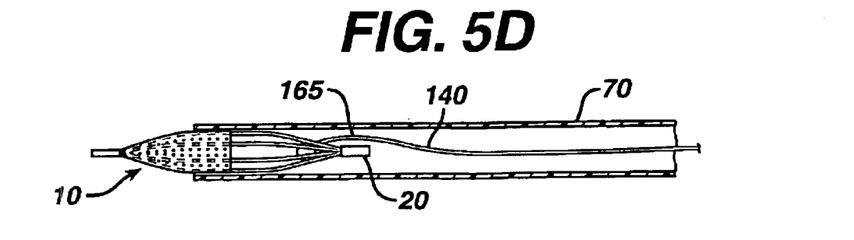

The releasable and retrievable vascular filter system further comprises a retrieval device for recapturing the filter, for causing the filter to achieve the smaller first diameter, and for removing the filter from the lumen. In this exemplary embodiment, the retrieval device comprises a ball hook retrieval system, as illustrated in FIG. 5A. The ball hook retrieval system 130 comprises a wire 140 having a proximal end 150 and a distal end 160, with a curve 165 near the distal end of the wire 140, and a ball 170 attached near the distal end of the wire 160. The ball hook retrieval system further comprises a receiver 180 near the proximal end 20 of the filter 10, as illustrated in FIG. 5B. The receiver 180 is accessed by inserting the ball 170 through the struts 40 of the filter 10, as illustrated in FIG. 5C. Then, the wire 140 and the filter 10 are retracted back into the catheter 70. The filter 10 collapses, as illustrated in FIG. 5D, and may then be withdrawn through the catheter 70.

As illustrated in FIGS. 1, 2, 3, 4A, 4B, 5A, 5B, 5C and 5D, the releasable and retrievable vascular filter system may be used to introduce, deploy and release a vascular filter into the lumen of a vessel, and then to retrieve the vascular filter from the lumen of a vessel. The catheter 70 may be introduced into the lumen of a vessel, until the distal end of the catheter 90 is positioned past the location of an occlusion in the vessel. Then, the distal end 30 of the filter 10 is inserted into proximal end 64 of the storage tube 65, until the storage tube completely covers the filter, as illustrated in FIG. 3. At this point, the distal end of the storage tube 66 is inserted into the proximal end of the catheter 70, as illustrated in FIG. 3. Then, the distal end 120 of the obdurator 100 is inserted into the proximal end of the storage tube 64 and advanced until it is substantially in contact with the proximal end of the filter 20. The obdurator 100 continues to be advanced until the filter 10 is pushed through the proximal end 80 of the catheter 70, through the catheter 70, and out of the distal end 90 of the catheter, as illustrated in FIG. 4B. The filter 10 then achieves its second larger diameter, as illustrated in FIG. 4B, and the anti-migration feature, in the form of the chronic outward force of the Nickel-Titanium alloy from which the filter is made, in this exemplary embodiment, allows the filter to remain substantially stationary in the lumen during the procedure. The filter captures embolic particulates generated during the procedure. The untethered filter 10 also allows the operator to perform guidewire exchanges, as needed throughout the procedure. After the interventional procedure is complete, the retrieval device, in the form of the ball hook retrieval system 130 in this exemplary embodiment, is introduced through the catheter 70, as illustrated in FIG. 5A. Once the ball 170 exits the distal end of the catheter 90, it is inserted through the filter struts 40, until it connects with the receiver 180, as illustrated in FIG. 5C. Then, the wire 140 is retracted back through the catheter 70, causing the filter 10 to collapse once it enters the catheter 70. Then, the filter 10 may be withdrawn from the body, with the embolic particulates captures therein.

The filter 10 may be made from any number of suitable materials, and is preferably made from Nickel-Titanium alloy. The filter 10 may comprise at least one marker band attached near the midpoints of the struts 40, at least one marker band attached near the distal end 30 of the filter, and at least one marker band attached near the proximal end 20 of the filter. The filter 10 may also comprise coatings or any other suitable means for enhancing the radiopacity of the device. The porous filter membrane 50 may be made from any number of suitable materials, and is preferably made from a flexible polymeric material with elastomeric properties chosen from a group consisting of polyurethane, polyethylene or a co-polymer thereof. The porous filter membrane 50 may comprise any number and configuration of pores and preferably comprises pores wherein the pore size is from about 20 to about 300 microns. The pores may be created by any suitable means, and may preferably be created by laser drilling. The storage tube 65 may be made from any number of suitable materials, and is preferably made from a polymeric material. The filter 10 may be loaded into the storage tube 65 at time of use, or may be preloaded, if the porous filter membrane 50 is made of a suitable material that does not take a permanent set. The catheter 70 may be made from any number of suitable materials, and is preferably made from a polymeric material. The obdurator 100 may be made from any number of suitable materials, and is preferably made from a polymeric material.

Figure 6A:
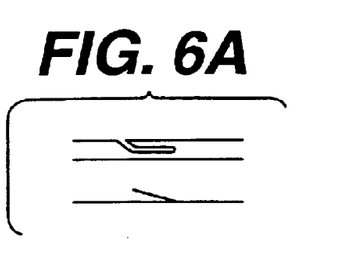
FIG. 6 illustrates a partial, simplified, top and sides view of exemplary embodiments of the releasable and retrievable vascular filter system, with suitable configurations of the anti-migration feature, in accordance with the present invention.
Figure 6B:
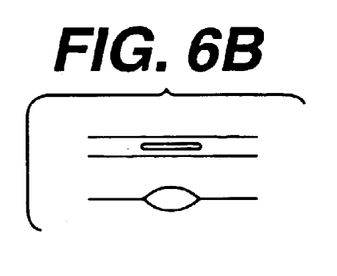
Figure 6C:
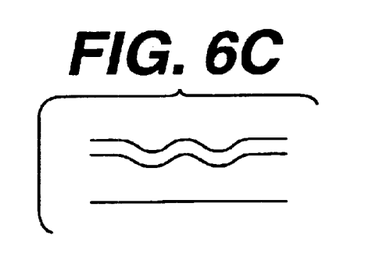
Figure 6D:
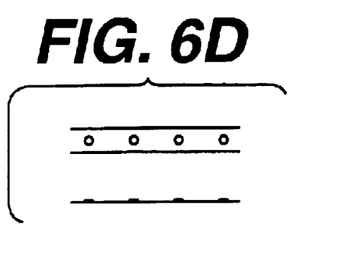
Figure 6E:
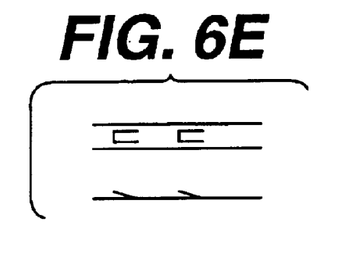

The anti-migration device may comprise any number of suitable configurations, including hooks, barbs (FIG. 6A), bowed features (FIG. 6B), zig-zags (FIG. 6C), dimples (FIG. 6D), and square barbs (FIG. 6E). The anti-migration feature may also comprise the chronic outward force of Nickel-Titanium alloy, from which the filter may be made, as illustrated in FIG. 1.

Figure 7A:
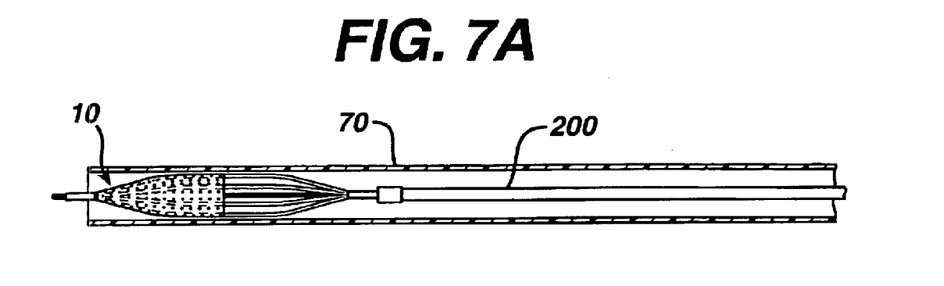
FIGS. 7A, 7B and 7C illustrate partial, enlarged, cross-sectional views of an exemplary embodiment of the releasable and retrievable vascular filter system, with the catheter being retracted to deploy the filter, in accordance with the present invention.
Figure 7B:
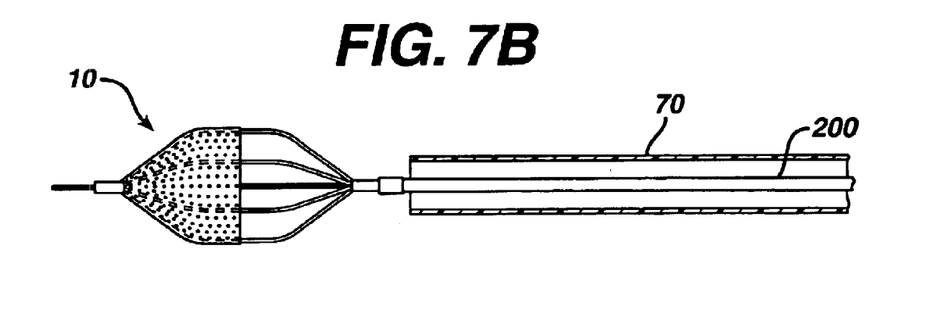
Figure 7C:
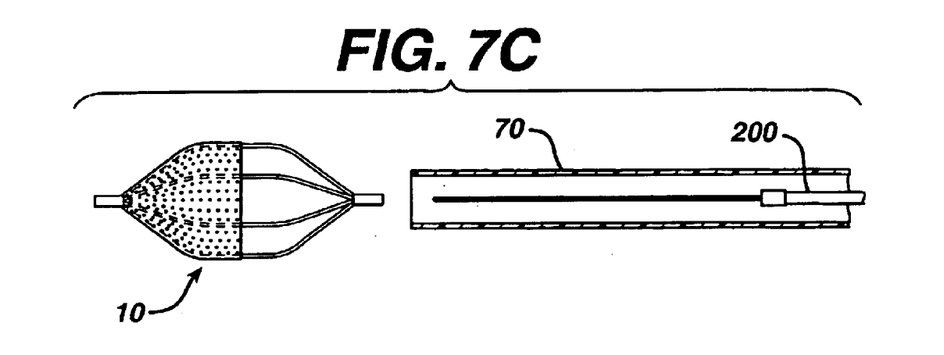
Figure 8A:
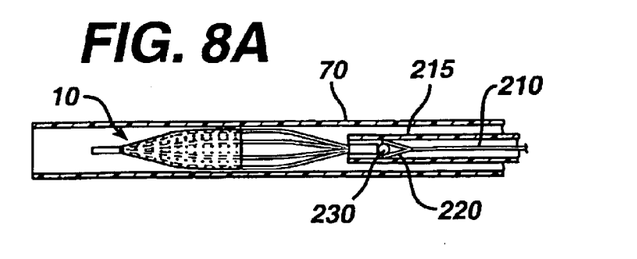
FIGS. 8A, 8B and 8C illustrate partial, enlarged, cross-sectional views of an exemplary embodiment of the releasable and retrievable vascular filter system, with the catheter being retracted and the guidewire disengaged, to deploy the filter, in accordance with the present invention.
Figure 8B:
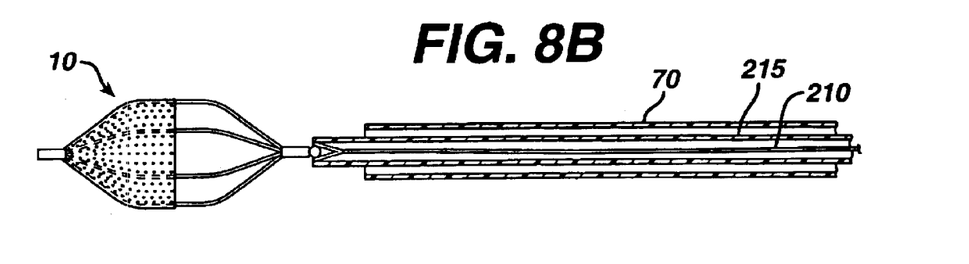
Figure 8C:
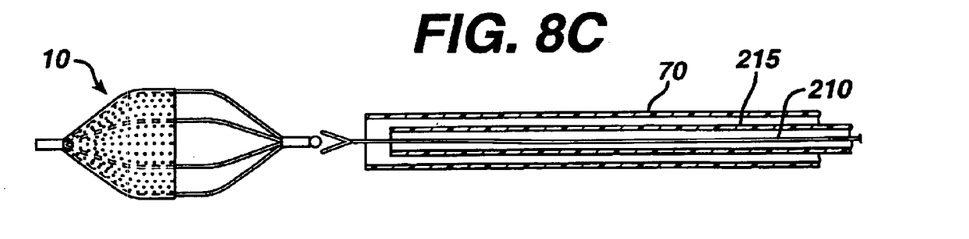
Figure 8D:
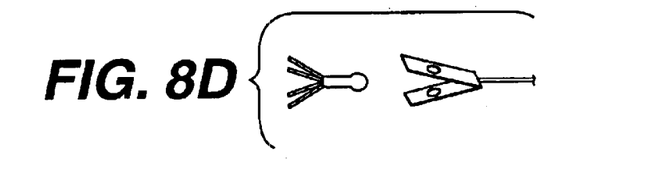
FIGS. 8D, 8E and 8F are partial, enlarged, cross-sectional views of exemplary embodiments of the mating features on the guidewire and filter, in accordance with the present invention.
Figure 8E:
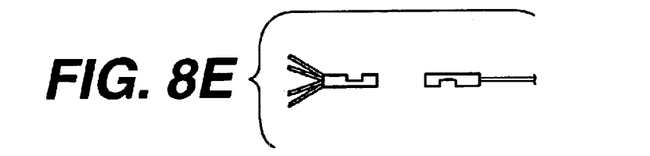
Figure 8F:
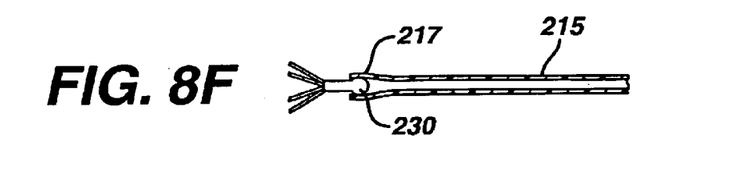

The deployment and release mechanism may comprise any number of suitable configurations, as illustrated in FIGS. 4A and 4B, which comprises a catheter and obdurator deployment system described above, and as illustrated in FIGS. 7 and 8. In FIG. 7A, the catheter 70 is coaxially disposed around a shaft 200, with the filter 10 attached near the distal end of the shaft 200. When the system is in position distal to the occlusion in the lumen of the vessel, the catheter 70, may be retracted, allowing the filter 10 to achieve the larger second diameter and to be placed in a generally sealing relationship with the lumen of the vessel, as illustrated in FIG. 7B. Then, the shaft 200 may be retracted to release the filter, as illustrated in FIG. 7C. In FIG. 8A, the catheter 70 is coaxially disposed around a sheath 215 and a guidewire 210, with the filter 10 attached near the distal end of the guidewire 210, via mating features 220 and 230, attached near the distal end of the guidewire 210, and near the proximal end of the filter 10. When the system is in position distal to the occlusion in the lumen of the vessel, the catheter 70 may be retracted, allowing the filter 10 to achieve the larger second diameter and to be placed in a generally sealing relationship with the lumen of the vessel, as illustrated in FIG. 8B. Then, the mating features 220 and 230 are disengaged by retracting the sheath 215 to release the filter, as illustrated in FIG. 8C. The mating features may be of any suitable configuration, and are preferably balls and holes, or mating slots, as illustrated in FIGS. 8D and 8E. The mating features may also release hydraulically, as illustrated in FIG. 8E, where the sheath 215 exhibits the characteristic that when fluid pressure is applied to the inner diameter, via a syringe or other suitable means, the walls of the distal section of the sheath 217 expand outwardly and release the mating feature 230, and hence the filter 10. The shaft may be made from any number of suitable materials, and is preferably made from a metallic material at the distal end and a polymeric material at the proximal end. The sheath may be made from any suitable material, and is preferably made from a polymeric material.

The wire may be made from any number of suitable materials, and is preferably made from Nickel-Titanium alloy. The snare may be made from any number of suitable materials, and is preferably made from Nickel-Titanium alloy.

Figure 9A:
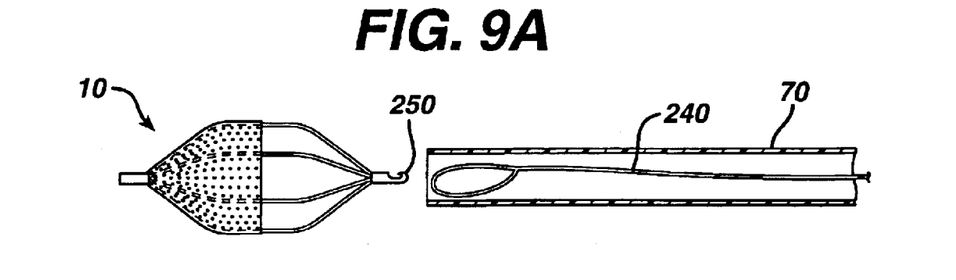
FIGS. 9A, 9B and 9C illustrate partial, enlarged, cross-sectional views of an exemplary embodiment of the releasable and retrievable vascular filter system, with a snare being used to retrieve the filter, in accordance with the present invention.
Figure 9B:
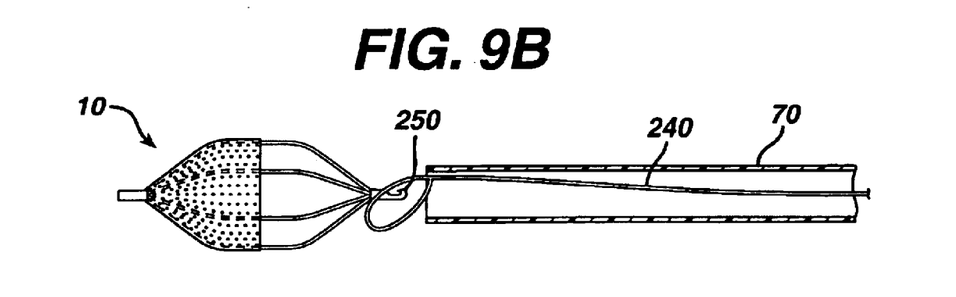
Figure 9C:
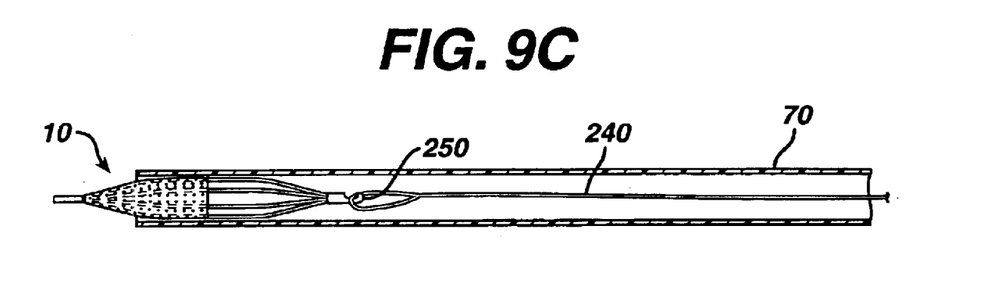
Figure 9D:
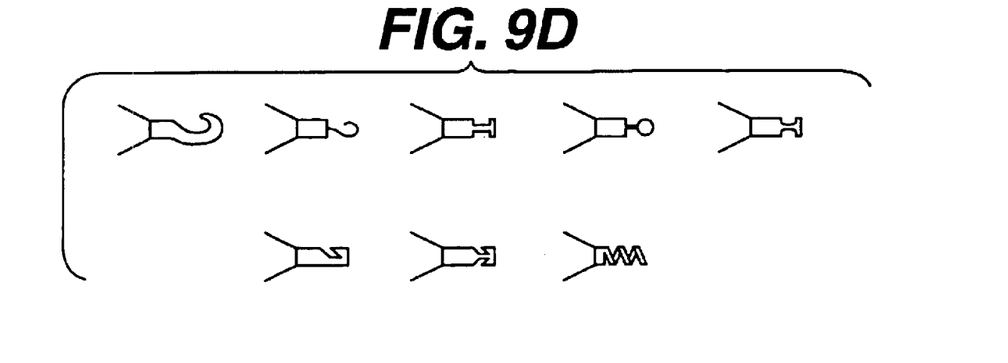
FIG. 9D illustrates a partial, enlarged, cross-sectional view of exemplary embodiments of the snareable feature on the filter, in accordance with the present invention.

The retrieval device may comprise any number of suitable configurations, as illustrated in FIGS. 5A, 5B and 5C, which comprise the ball hook retrieval system, and FIGS. 8A, 8B, 8C and 8D, which comprise a mating hook system. The retrieval device may also comprise a snare 240 and a snareable feature 250 on the filter, as illustrated in FIG. 9. The snare 240 in introduced through a catheter, as illustrated in FIG. 9. The loop of the snare 250 exits the catheter and attaches itself to the snareable feature 250, on the filter 10, which is a hook in this exemplary embodiment. The snare 240 is then retracted back into the catheter 70, dragging the filter 10 into the catheter 70, and causing the filter to achieve its smaller first diameter, as illustrated in FIG. 9C. The snareable feature may comprise any number of suitable configurations, as illustrated in FIG. 9D, and may comprise hooks, knobs, slots or coils.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to include all modifications that may fall within the scope of the appended claims.

We claim:

1. A guidewireless vascular filter system for insertion into a lumen of a vessel, said system comprising:
  a) a free standing, guidewireless filter support structure comprising a proximal portion, a distal portion, and a plurality of struts extending therebetween, said struts further comprising proximal portions and distal portions, said filter having a smaller first diameter for insertion into said lumen, and a second larger diameter for expanding to a diameter substantially equal to the diameter of said lumen and to be placed in a generally sealing relationship with said lumen;
  b) a porous filter membrane connected to said filter distal portion and said plurality of struts;
  c) deploying and releasing means operatively associated with said filter support structure, said deploying and releasing means causing said filter to be positioned in said lumen of said vessel, and causing said filter to achieve said larger second diameter;
  d) anti-migration means associated with said filter support structure, said anti-migration means causing said filter to remain substantially stationary in said lumen of said vessel; and
  e) retrieving means operatively associated with said filter support structure, said retrieving means allowing recapture of said filter, causing said filter to achieve said smaller first diameter, and allowing removal of said filter from said lumen.

2. The vascular filter system according to claim 1, wherein said filter support structure is made from Nickel-Titanium alloy.

3. The vascular filter system according to claim 2, wherein said anti-migration means comprises the chronic outward force of said Nickel-Titanium alloy.

4. The vascular filter system according to claim 1, wherein said filter support structure further comprises means to enhance the radiopacity of the device.

5. The vascular filter system according to claim 1, wherein said porous filter membrane is made from a polymeric material chosen from a group consisting of polyurethane, polyethylene or a co-polymer thereof.

6. The vascular filter system according to claim 5, wherein the pore size of said porous filter membrane is in the range of from about 20 to about 300 microns.

7. The vascular filter system according to claim 1, wherein said deploying means comprises a storage tube having an proximal end and a distal end and an inner lumen, with said distal end of said filter slidably insertable into said proximal end of said storage tube; said deploying means further comprising a catheter having an outer diameter and an inner diameter, a proximal end and a distal end, and an inner lumen, with said distal end of storage tube containing said filter slidably insertable into said proximal end of said catheter; said deploying means further comprising an obdurator having an outer diameter, a proximal end and a distal end, with said distal end of said obdurator slidably insertable into said proximal end of said storage tube until said distal end of said obdurator is substantially in contact with said proximal end of said filter, and said obdurator is positioned to push said filter into said proximal end of said catheter, through said lumen of said catheter, and out of said distal end of said catheter.

8. The vascular filter system according to claim 7, wherein said storage tube is made from a polymeric material.

9. The vascular filter system according to claim 7, wherein said catheter is made from a polymeric material.

10. The vascular filter system according to claim 7, wherein said obdurator is made from a polymeric material.

11. The vascular filter system according to claim 1, wherein said deploying means comprises a catheter having an outer diameter and an inner diameter, a proximal end and a distal end, and an inner lumen, said deploying means further comprising a shaft having an outer diameter, a proximal end and a distal end, with said filter releasably attached near and detachable from said distal end of said shaft, and said catheter coaxially disposed around said shaft and said filter, such that said catheter may be slidably retracted to deploy said filter.

12. The vascular filter system according to claim 11, wherein said catheter is made from a polymeric material.

13. The vascular filter system according to claim 11, wherein said distal end of said shaft is made from a metallic material and said proximal end of said shaft is made from a polymeric material.

14. The vascular filter system according to claim 1, wherein said deploying means comprises a guidewire having a proximal end and a distal end, with said proximal end of said filter releasably attachable near and detachable from said distal end of said guidewire; said deploying means further comprising a catheter having an outer diameter and an inner diameter, a proximal end and a distal end, and an inner lumen, with said proximal end of said guidewire slidaby insertable into said distal end of said catheter until said catheter is coaxially disposed around said guidewire and said filter, and said catheter may be slidably retracted to deploy said filter.

15. The vascular filter system according to claim 14, wherein said guidewire is made from Nickel-Titanium alloy.

16. The vascular filter system according to claim 14, wherein said catheter is made from a polymeric material.

17. The vascular filter system according to claim 1, wherein said retrieving means comprises a guidewire detachable from and attachable to said filter.

\* \* \* \* \*